United States Patent [19]
Phillips

[11] Patent Number: 6,057,755
[45] Date of Patent: May 2, 2000

[54] AUTOMOTIVE CARBON MONOXIDE DETECTION SYSTEM

[76] Inventor: Frances Phillips, 7425 Colton La., Manassas, Va. 20109

[21] Appl. No.: 09/078,887

[22] Filed: May 14, 1998

[51] Int. Cl.[7] .................................................. B60Q 1/00
[52] U.S. Cl. ..................... 340/438; 340/632; 200/85 A; 180/271; 180/273; 180/279
[58] Field of Search ..................... 340/438, 632, 340/430; 180/271, 273, 279; 200/85 R, 85 A

[56] References Cited

U.S. PATENT DOCUMENTS

| | | | |
|---|---|---|---|
| 3,786,462 | 1/1974 | Hayden | 340/237 R |
| 3,974,040 | 8/1976 | Siebke et al. | 204/1 |
| 4,446,345 | 5/1984 | Sheiry | 200/85 R |
| 4,464,651 | 8/1984 | Duhame | 340/521 |
| 5,066,466 | 11/1991 | Hölter et al. | 422/98 |
| 5,333,703 | 8/1994 | James et al. | 180/271 |
| 5,576,739 | 11/1996 | Murphy | 340/825.06 |
| 5,694,118 | 12/1997 | Park et al. | 340/632 |
| 5,739,756 | 4/1998 | Margulies | 340/632 |

*Primary Examiner*—Daniel J. Wu
*Assistant Examiner*—Julie B. Lieu
*Attorney, Agent, or Firm*—Henderson & Sturm

[57] ABSTRACT

A vehicle carbon monoxide detection system 10 including internal 20 and external 40 carbon monoxide sensors operatively associated with the vehicle cab 150 and connected to a computer 60 that will selectively activate one of the sensors 20, 40 in response to the output of the vehicle speedometer 100. When the selected sensor 20, 40 detects excess carbon monoxide fumes relative to the vehicle cab 150, the computer will deactivate the vehicle ignition switch 110 stopping the vehicle motor 120 which is the source of the carbon monoxide fumes.

7 Claims, 1 Drawing Sheet

AUTOMOTIVE CARBON MONOXIDE DETECTION SYSTEM

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of carbon monoxide detection systems in general, and in particular to a carbon monoxide detection system coupled to a vehicle ignition to cut off the vehicle motor in response to the output of internally and externally mounted sensors.

2. Description of Related Art

As can be seen by reference to the following U.S. Pat. Nos. 3,786,462; 5,066,466; 5,576,739; and 5,694,118, the prior art is replete with myriad and diverse carbon monoxide detector systems.

While all of the aforementioned prior art constructions are more than adequate for the basic purpose and function for which they have been specifically designed, they are uniformly deficient with respect to their failure to provide a simple, efficient, and practical carbon monoxide detector system that is tied into a vehicle ignition to terminate the generation of the carbon monoxide fumes in response to the readings from sensors mounted both on the interior and exterior of a vehicle cab.

As most people are no doubt aware, elevated levels of carbon monoxide fumes in a closed space can have both short term and sometimes fatal effects on individuals exposed to high concentrations of the gas.

While the short term effects of low levels of carbon monoxide poisoning are not immediately life threatening, they do represent a potentially lethal threat due to the diminished physical and mental capacities of the operator of the vehicle which may have a direct probative cause that leads to a vehicular accident resulting in death and or injury not only to the occupants of the vehicle subject to the elevated levels of carbon monoxide fumes, but also to innocent bystanders including the occupants of other vehicles.

In addition, there are also numerous recorded instances wherein someone leaves an unattended vehicle running in an attached garage with the result that all of the occupants of the house are overcome and succumb to these deadly fumes.

As a consequence of the foregoing situation, there has existed a longstanding need for a new and improved automotive carbon monoxide detection system that monitors the carbon monoxide levels both internally and externally of a vehicle cab and shuts off the ignition of the vehicle in response to selected threshold levels of carbon monoxide, and the provision of such a construction is a stated objective of the present invention.

BRIEF SUMMARY OF THE INVENTION

Briefly stated, the vehicle carbon monoxide detection system that forms the basis of the present invention comprises in general, internal and external carbon monoxide sensors operatively associated with the cab of a vehicle and operatively connected to a computer that will deactivate the vehicle ignition switch to stop the vehicle motor in response to the output of one or more of the carbon monoxide sensors.

As will be explained in greater detail further on in the specification, the external carbon monoxide sensor is only activated when the vehicle speedometer indicates that the vehicle is not moving and the weight of the driver is not sensed by a weight sensor incorporated into the driver's seat and connected to the computer.

In addition, the internal carbon monoxide sensor is further provided with a time delay mechanism that will only activate the internal sensor upon the speedometer registering a predetermined minimum speed and a selected time interval elapsing as measured by the time delay mechanism.

In both instances, the computer will shut down the engine which is the primary source of carbon monoxide fumes when either of the carbon monoxide sensors detect excess levels of carbon monoxide relative to the vehicle cab.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
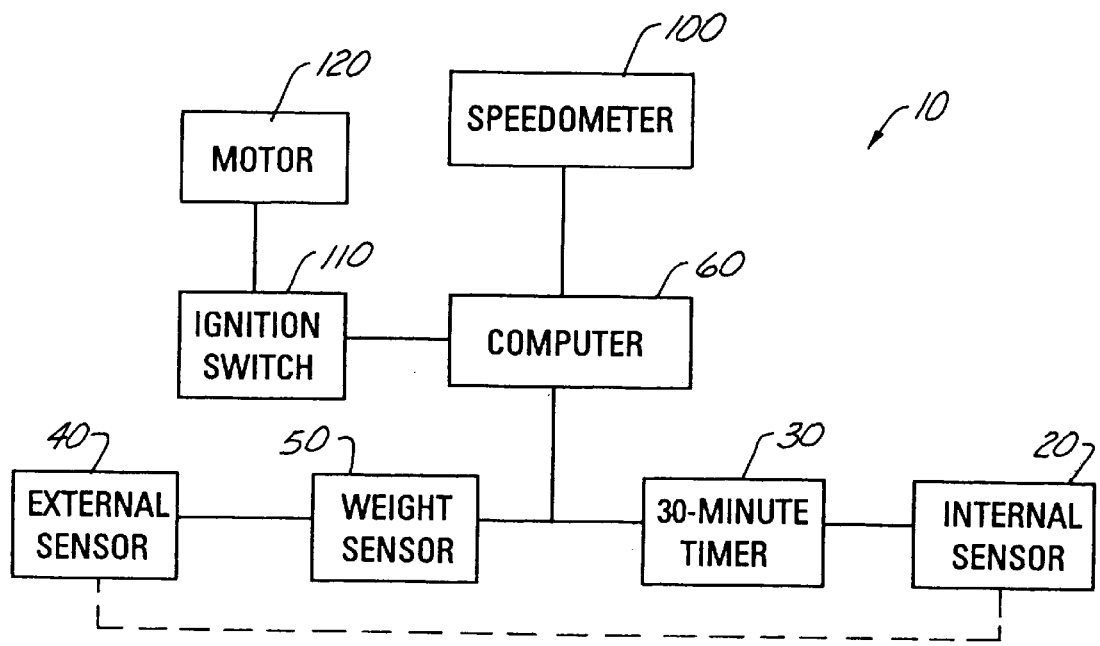
FIG. 1 is a schematic view of the carbon monoxide sensor system that forms the basis of the present invention.

As can be seen by reference to the drawings, and in particularly to FIG. 1, the automotive carbon monoxide detection system that forms the basis of the present invention is designated generally by the reference number 10. The system 10 comprises in general, an internal carbon monoxide sensor 20 coupled to a time delay mechanism 30 and an external carbon monoxide sensor 40 coupled to a weight sensor 50 wherein the outputs from both the internal sensor 20 and the external sensor 40 are fed into a computer processor unit (CPU) 60 that is responsive to the output of a vehicle speedometer 100 to selectively activate the internal 20 or external 40 sensor as will be explained in greater detail further on in the specification.

In addition, the CPU 60 is also operatively connected to the vehicle ignition switch 110 which controls the operation of the vehicle motor 120.

In the preferred embodiment of the invention illustrated in the drawings, the internal carbon monoxide sensor 20 is activated once the speedometer registers a minimum selected speed (e.g., 15 MPH) and a selected interval of time has elapsed as determined by the time delay mechanism 30 (e.g., 30 minutes) wherein the internal sensor 20 will remain energized until the ignition switch 110 is turned off.

On the other hand, the external carbon monoxide sensor 40 is activated once the speedometer 100 registers the fact that the vehicle is not moving, the motor 120 is running, and the weight sensor 50 indicates that the driver is not sitting in the driver's seat 140.

In the first instance, the time delay mechanism 30 is employed to prolong the useful life of the system 10 in that under most circumstances, dangerous levels of carbon monoxide fumes will not build up within the interior of the vehicle cab 150 until a predetermined period of time has elapsed such as would be encountered on long trips.

In the second instance, the exterior ambient levels of carbon monoxide normally do not affect the operator of a vehicle while the vehicle is in motion. However, in those instances wherein the vehicle operator leaves the vehicle running and unattended in a closed space, it is imperative that the external carbon monoxide sensor 40 be activated to prevent the buildup of toxic carbon monoxide levels both within the enclosed space and adjacent structures for obvious reasons.

It should also be noted that in many instances the provision of only an internal carbon monoxide sensor 20 will be inadequate to address the problem of an unattended running vehicle scenario in that due to the relatively air tight construction and/or elevation of certain vehicle cabs, toxic levels of carbon monoxide can be generated and dispersed on the exterior of the vehicles. The levels of carbon monoxide within the vehicle cab 150 may remain well below the threshold levels required for the internal carbon monoxide detector 20 to send a signal to the CPU 60 to turn off the vehicle ignition 110 to cease the generation of carbon monoxide fumes from the motor 120.

Figure 2:
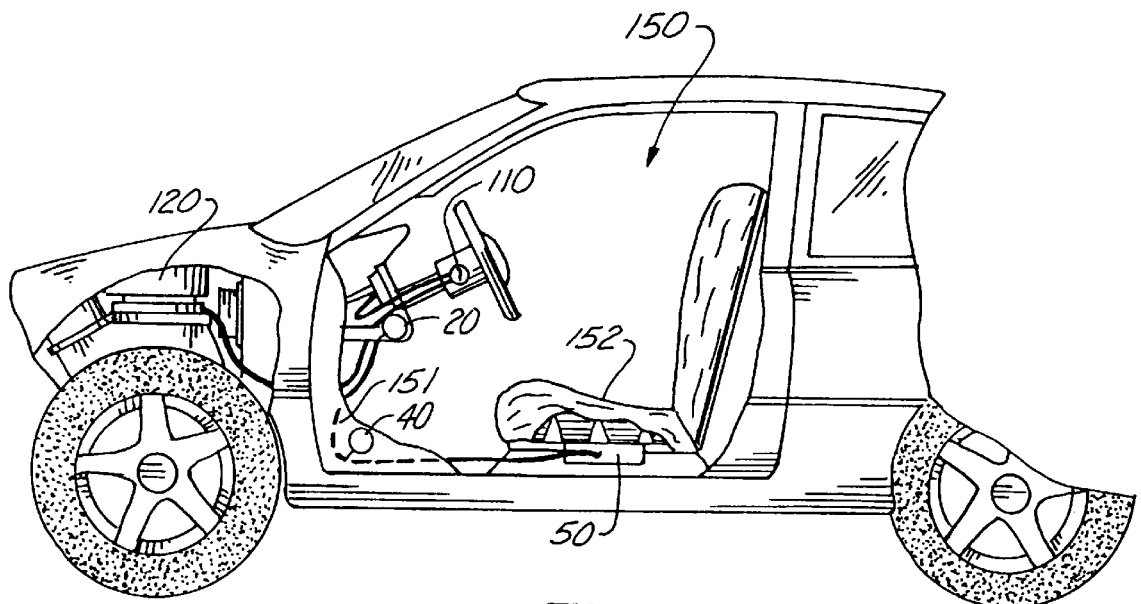
FIG. 2 is a partial cut-away view of a motor vehicle equipped with the carbon monoxide sensor system of this invention.

As a consequence of the foregoing situation, this invention also contemplates positioning the interior 20 and exterior 40 carbon monoxide sensors fairly low relative to the vehicle cab 150 and while FIG. 2 shows the internal sensor 20 mounted on the lower portion of the vehicle dashboard, in the preferred embodiment of the invention both of the sensors 20 and 40 would be mounted on the lower portion of the vehicle's driver side door 151 preferably in a single aperture (not shown) that extended completely through the vehicle door 151.

In this way, the interior carbon monoxide sensor 20 is not only positioned well below the level of the driver's head, but is also positioned beneath the level of a child's head, which would be subject to the adverse effects of the carbon monoxide fumes substantially sooner than that of an adult.

In addition, as depicted by the dashed lines in FIG. 1, it is also contemplated that the internal sensor 20 may be optionally coupled to the external sensor 40 in order to defeat a suicide attempts by an individual who would try to avoid the failsafe feature of this system 10 by sitting either in one of the passenger seats as opposed to the weight sensor bearing driver's seat 152.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

I claim:

1. A carbon monoxide detection system for vehicles having a motor controlled by an ignition switch, a speedometer, and a vehicle cab equipped with a driver's seat wherein the detection system comprises;

an internal carbon monoxide sensor mounted on the interior of the vehicle cab;

a computer operatively associated with both the internal carbon monoxide sensor and said ignition switch for terminating the operation of the vehicle motor in response to the levels of carbon monoxide gas sensed by said internal carbon monoxide sensor within the interior of the vehicle cab;

an external carbon monoxide sensor mounted on the exterior of the vehicle cab and operatively associated with said computer and said ignition switch for termination of the operation of the vehicle motor in response to the levels of carbon monoxide gas sensed by the external carbon monoxide sensor on the exterior of the vehicle cab wherein said computer is operatively associated with said speedometer and both the internal and external carbon monoxide sensors to activate said internal carbon monoxide sensor in response to a selected output from said speedometer, and to activate said first external carbon monoxide sensor in response to a second selected output from said speedometer; and, a time delay mechanism interposed between said computer and said internal carbon monoxide sensor for delaying the activation of the internal carbon monoxide sensor in response to the first selected output from said speedometer.

2. The detection system as in claim 1; wherein the first selected output from the speedometer and the second selected output from the speedometer are different.

3. The detection system as in claim 1; wherein the first selected output from the speedometer and the second selected output from the speedometer are the same.

4. The detection system as in claim 1 further including:

a weight sensor operatively associated with the driver's seat and interposed between said computer and said external carbon monoxide sensor for selectively blocking the activation of the external carbon monoxide sensor in response to another selected output from said speedometer.

5. The detection system as in claim 4 wherein the weight sensor must register the absence of the driver's weight on the driver's seat and the speedometer must register that the vehicle is not moving before the external carbon monoxide sensor is activated.

6. A carbon monoxide detection system for vehicles having a motor controlled by an ignition switch, a speedometer, and a vehicle cab equipped with a driver's seat wherein the detection system includes:

an external carbon monoxide sensor mounted on the exterior of the vehicle cab;

a computer operatively associated with both the external carbon monoxide sensor and said ignition switch for terminating the operation of the vehicle motor in response to the levels of carbon monoxide gas sensed by said external carbon monoxide sensor within the exterior of the vehicle cab;

an internal carbon monoxide sensor mounted on the interior of the vehicle cab and operatively associated with said computer and said ignition switch for termination of the operation of the vehicle motor in response to the levels of carbon monoxide gas sensed by the internal carbon monoxide sensor on the interior of the vehicle cab wherein said computer is operatively associated with said speedometer and both the internal and external carbon monoxide sensors to activate said internal carbon monoxide sensor in response to a first selected output from said speedometer, and to activate said external carbon monoxide sensor in response to a second selected output from said speedometer;

a weight sensor operatively associated with the driver's seat and interposed between said computer and said external carbon monoxide sensor for selectively blocking the activation of the external carbon monoxide sensor in response to the second selected output from said speedometer; wherein the first selected output from the speedometer and the second selected output from the speedometer are the same.

7. The detection system as in claim 6 further comprising:

a time delay mechanism interposed between said computer and said internal carbon monoxide sensor for delaying the activation of the internal carbon monoxide sensor in response to the first selected output from said speedometer.

\* \* \* \* \*